| United States Patent [19] | [11] | 4,384,134 |
|---|---|---|
| Schulz et al. | [45] | May 17, 1983 |

[54] PROCESS FOR PREPARING ORGANIC ACIDS

[75] Inventors: Johann G. Schulz, Pittsburgh; Daniel Margosian, Verona, both of Pa.

[73] Assignee: Gulf Research & Development Company, Pittsburgh, Pa.

[21] Appl. No.: 290,662

[22] Filed: Aug. 6, 1981

[51] Int. Cl.³ .......................................... C07C 51/275
[52] U.S. Cl. ..................................... 562/410; 562/407
[58] Field of Search ................................ 562/407, 410

[56] References Cited

U.S. PATENT DOCUMENTS 4,052,448 10/1977 Schulz et al. ...................... 562/407

Primary Examiner—Robert Gerstl
Attorney, Agent, or Firm—Deane E. Keith; Forrest D. Stine; Joseph J. Carducci

[57] ABSTRACT

A process for preparing a coal derivative comprising a mixture of monocyclic, polycyclic, multifunctional carboxylic acids which comprises contacting an aqueous slurry containing coal with aqueous nitric acid and then drying the resulting product to remove water therefrom.

17 Claims, No Drawings

PROCESS FOR PREPARING ORGANIC ACIDS

BACKGROUND OF THE INVENTION

1. Field of the Invention

This invention relates to a process for preparing a coal derivative comprising a mixture of monocyclic, polycyclic, multifunctional carboxylic acids which comprises contacting coal with aqueous nitric acid and then drying the resulting product to remove water therefrom. Preferably the process involves contacting a portion of the coal to be treated with aqueous nitric acid and then adding the remainder of the coal to the reaction mixture prior to the end of the reaction period.

2. Description of Prior Art

In U.S. Pat. No. 4,052,448 of Schulz et al, dated Oct. 4, 1977, there is disclosed a process for preparing coal derivatives which comprises subjecting a slurry containing coal to reaction with aqueous nitric acid, mechanically separating the solids in the resulting slurry to obtain a mixture of water-insoluble coal derivatives and a mixture of water-soluble coal derivatives. The water-insoluble coal derivatives are then separated into a solvent-soluble, water-insoluble fraction and a solvent-insoluble, water-insoluble fraction. In the specific examples therein the reaction product is subjected to filtration to separate the water-insoluble coal derivatives therefrom. Unfortunately, such filtration, or other mechanical separation that is contemplated therein, is cumbersome, time consuming and expensive.

SUMMARY OF THE INVENTION

We have found that if instead of subjecting the reaction product to mechanical separation to remove water-insoluble coal derivatives therefrom, the reaction product is subjected to a drying operation to remove water therefrom, the above problems associated with mechanical separation are eliminated. In a preferred embodiment, we have unexpectedly found that the separation of water from the reaction product is facilitated by bringing only a portion of the coal into contact with the nitric acid at the beginning of the reaction period and then adding the remainder of the coal to the reaction product prior to the end of the reaction period. We have additionally unexpectedly found that by carrying out the process as defined and claimed herein nitric acid utilization is far higher and the total amounts of solvent-soluble and water-soluble coal derivatives is substantially in excess of the amounts of the same obtained in said U.S. Pat. No. 4,052,448 of Schulz et al.

The coal derivative mixtures resulting from the novel process defined and claimed herein, in whole, or in part, are substantially soluble in water, polar solvents, such as methanol, ethanol, acetone, tetrahydrofuran, etc., combinations of polar solvents and/or combinations of water and polar solvents. Examples of such combinations that can be used include methanol and ethanol, at least one of methanol and ethanol with acetone, and at least one of methanol, ethanol, acetone and tetrahydrofuran with water. The individual components of said mixtures are believed to comprise condensed and/or noncondensed cyclic structures, such as benzene rings, with an average number of said rings in the individual molecules ranging from one to about 10, but generally from one to about eight. On the average, the number of carboxyl groups carried by the individual molecules will range from about two to about 20, generally from about three to about 10, and the average number of nitro groups from about one to about ten, generally from about two to about six. The average molecular weight of the mixture will range from about 400 to about 2000, generally from about 700 to about 1000, and the average neutral equivalent will range from about 80 to about analysis of the novel mixture is defined below in Table I in approximate amounts.

TABLE I

|          | Weight Percent |                  |
|----------|----------------|------------------|
|          | Broad Range    | Preferred Range  |
| Carbon   | 50 to 60       | 52 to 56         |
| Hydrogen | 3 to 5         | 3.6 to 4.4       |
| Nitrogen | 3 to 6         | 4 to 5           |
| Oxygen   | 25 to 45       | 30 to 40         |
| Sulfur   | 0.2 to 0.5     | 0.3 to 0.5       |
| Ash      | 0.1 to 5       | 0.3 to 3         |

In carrying out the reaction herein the components of the reaction must include coal, nitric acid and water wherein the weight ratios thereof are in the range of about 1:10:1 to about 1:0.1:10, preferably about 1:5:1 to about 1:0.5:5. The defined weight ratios are based on substantially moisture-free, ash-free coal and 100 percent nitric acid. The nitric acid that is used will be an aqueous nitric acid having a concentration of about five to about 90 percent, preferably about 10 to about 70 percent.

The coal that can be used herein can have the following composition on a moisture-free basis:

TABLE II

|          | Weight Percent |                  |
|----------|----------------|------------------|
|          | Broad Range    | Preferred Range  |
| Carbon   | 45–95          | 60–92            |
| Hydrogen | 2.5–7          | 4–6              |
| Oxygen   | 2.0–45         | 3–25             |
| Nitrogen | 0.75–2.5       | 0.75–2.5         |
| Sulfur   | 0.3–10         | 0.5–6            |

The carbon and hydrogen content of the coal will reside primarily in multi-ring aromatic compounds (condensed and/or uncondensed), heterocyclic compounds, etc. Oxygen and nitrogen are believed to be present primarily in chemical combination. Some of the sulfur is believed to be present in chemical combination with the aromatic compounds and some in chemical combination with inorganic elements associated therewith, for example, iron and calcium.

In addition to the above the coal being treated herein will also contain solid, primarily inorganic, compounds which will not be converted to the desired organic mixture claimed herein, which are termed ash, and are composed chiefly of compounds of silicon, aluminum, iron and calcium, with smaller amounts of compounds of magnesium, titanium, sodium and potassium. The ash content of the coal treated herein will amount to less than about 50 weight percent, based on the moisture-free coal, but, in general, will amount to about 0.1 to about 30 weight percent, usually about 0.5 to about 20 weight percent.

Anthracitic, bituminous and subbituminous coal, lignitic materials, and other types of coal products referred to in ASTM D-388 are exemplary of coals that can be treated in accordance with the process defined herein to produce the desired organic mixture. Some of these coals in their raw state will contain relatively large amounts of water. These can be dried prior to use herein. The coal, prior to use, is preferably ground in a suitable attrition machine, such as a hammermill, to a size such that at least about 50 percent of the carbonaceous material will pass through a 40-mesh (U.S. Series) sieve. If desired, the coal can be treated, prior to reaction herein, using any conventional means, to remove therefrom any materials forming a part thereof that will not be converted in reaction with nitric acid herein.

The reaction mixture defined above is mixed while being maintained at a temperature of about 15° to about 200° C., preferably about 50° to about 100° C., and a pressure of about atmospheric to about 1000 pounds per square inch gauge (about 100 to about 6900 kPa), or even higher, but preferably about atmospheric to about 500 pounds per square inch gauge (about 100 to about 3450 kPa), for about 0.5 to about 15 hours, preferably about two to about six hours.

In the preferred embodiment herein not all of the coal that is to be contacted with nitric acid is present during the principal reaction period. Thus, from about 60 to about 90 weight percent, preferably from 70 to about 80 weight percent of the coal, is present during the principal reaction period, that is, generally, at the beginning of the reaction period, and the remainder can be added all at once, or incrementally, to the reaction mixture following the principal reaction period, but generally within a period of about 0.5 to about 10 hours, preferably about one to about five hours, following the principal reaction period.

At the end of the reaction period the product is subjected to a drying operation, for example, at a temperature of about 25° to about 150° C., preferably about 50° to about 100° C., and a pressure of about atmospheric to about one millimeter of mercury. As a result of such drying operation, substantially all of the water is removed from the reaction product and, additionally, unreacted nitric acid, if present. Nitric acid, if present, will be extremely small, since we have found that by carrying out the operation, as defined, we obtain substantially complete nitric acid utilization.

In order to obtain the excellent results desired herein, preferably to avoid decarboxylation and perhaps denitrofication, it is essential that the parameters defined above be substantially adhered to.

The recovery of coal derivatives soluble in polar solvents from the dried product can be carried out in any suitable or conventional manner, preferably by extraction. Thus in a preferred procedure extraction is effected using polar solvents, combinations of polar solvents, combinations of polar solvents and water, etc. We have found that extremely good results have been obtained using methanol, ethanol, acetone and tetrahydrofuran. The extraction can be carried out by contacting the solid reaction product obtained at the end of the drying period with the polar solvent wherein the weight ratios of solid reaction product to polar solvent can be, for example, in the range of about 10:1 to about 1:10, preferably about 5:1 to about 1:5. Although the extraction can be carried out at elevated pressures, for example, upto about 500 pounds per square inch gauge (3450 kPa), atmospheric pressure is preferred. Temperatures can be in the range of about 25° to about 150° C., preferably about 35° to about 100° C.

The recovery of the desired coal derivative mixture from the resulting solution can be effected by heating the same at a temperature of about 25° upto the boiling point of the solvent, and a pressure of about atmospheric to about one millimeter of mercury to remove the polar solvent therefrom.

Left behind after removal of the desired resulting solution from the reaction product can be polar-solvent insoluble coal intermediates and ash.

The coal derivatives obtained herein can be used for the same purposes that the coal derivatives obtained in said U.S. Pat. No. 4,052,448 have been used. In a preferred embodiment, the coal derivative mixtures obtained herein are used in preparing resins as defined and claimed in out U.S. patent application Ser. No. 290,663, entitled Novel Composition and Process for Producing Solid Resin Therefrom, filed concurrently herewith.

DESCRIPTION OF PREFERRED EMBODIMENTS

In each of the four examples described below a German Braunkohle was used having the following analysis, on a moisture-free basis: 64.37 weight percent carbon, 5.06 weight percent hydrogen, 25.09 weight percent oxygen, 0.14 weight percent sulfur, 0.605 weight percent nitrogen and 3.88 weight percent ash. The coal contained 10 weight percent water. Example I describes an embodiment of the process defined and claimed herein, while Example II describes a preferred embodiment of the process defined and claimed herein.

EXAMPLE I

To a flask containing 70 grams of 70 weight percent aqueous nitric acid, there was added over a period of 55 minutes a slurry containing 51.0 grams, on a moisture-free and ash-free basis, of the above coal and 115 grams of water. During the operation the contents were constantly stirred and maintained at atmospheric pressure and at a temperature of 55° C. At the end of the addition period, the contents of the flask were maintained at 55° C. for an additional hour. During the operation any nitrogen oxides that may have formed were permitted to escape from the reaction zone. At the end of the reaction the contents of the flask were subjected to a vacuum of 28 inches of mercury and 42° C. to remove water therefrom and the water was analyzed for its nitric acid concentration and was found to have a nitric acid concentration of 11.5 percent. The remaining solids, amounting to 65.5 grams, were exhaustively extracted at ambient temperature and pressure with methanol. The extract was subjected to a vacuum of 28 inches of mercury and about 13° C. to remove methanol therefrom. The amount of solvent-insoluble coal derivative amounted to 20.3 grams, while the amount of solvent-soluble coal derivative amounted to 40.9 grams.

EXAMPLE II

This example is similar to Example I except that the coal was added to the reaction zone in two separate stages. In the first stage the slurry added to the nitric acid in the flask contained 42.0 grams of coal, on a moisture-free and ash-free basis, and 90 grams of water. This time the holding period after the addition of the slurry was one-half hour. At the end of the one-half hour holding period there was added to the reactor contents a second slurry containing nine grams of coal, on a moisture-free basis, and 25 grams of water over a ten-minute period while the temperature was maintained at 55° C., as in the first stage addition. The contents of the reactor were held at one hour at 55° C. The product was then worked up as in Example I. Whereas some foaming occurred during the course of the slurry addition period and during the evaporation stage of Example I, which required constant attention, no foaming problems were noticeable herein.

Example III below was carried out following the procedure described in U.S. Pat. No. 4,052,448, referred to hereinabove.

EXAMPLE III

The reaction stage described in Example I was repeated. Instead of subjecting the reactor contents to a drying step as in Example I, the reactor contents herein were subjected to filtration. The water was removed from the aqueous filtrate by subjecting it to a vacuum of 28 inches of mercury at 42° C. and the distillate was analyzed for its nitric acid content. The water-soluble solid portion remaining was analyzed for its ash content and for its water-soluble coal derivative content. The water-insoluble portion remaining after filtration was exhaustively extracted with methanol, following the procedure of Example I, to recover solvent-soluble coal derivatives.

EXAMPLE IV

Example III was repeated, except that the nitric acid reaction stage was identical to the procedure used in Example II.

The data obtained above are summarized below in Table I.

was only 64.0 and 65.0 percent, respectively. Similarly, the concentration of nitric acid in the aqueous fraction to be disposed at the end of the reaction was substantially lower in Examples I and II than in Examples III and IV.

Obviously, many modifications and variations of the invention, as hereinabove set forth, can be made without departing from the spirit and scope thereof, and therefore only such limitations should be imposed as are indicated in the appended claims.

We claim:

1. A process for preparing a coal derivative comprising a mixture of monocyclic, polycyclic, multifunctional carboxylic acids which comprises contacting an aqueous slurry containing coal with aqueous nitric acid, wherein the weight ratios of said coal, nitric acid and water are in the range of about 1:10:1 to about 1:0.1:10 and said contact is effected in the temperature range of about 15° to about 200° C. for about 0.5 to about 15 hours, and then drying the resulting product at a pressure of about atmospherhic to about one millimeter of mercury and a temperature of about 25° to about 150° C. to remove water therefrom.

2. The process of claim 1 wherein the weight ratios of said coal, nitric acid and water are in the ranges of about 1:5:1 to about 1:0.5:1.

3. The process of claim 1 wherein said contact is

TABLE I

| | Example No. | | | |
|---|---|---|---|---|
| | I | II | III | IV |
| | | Mode | | |
| Reactor Components | Evaporation (One-Step Addition) | Evaporation (Multiple-Step Addition) | Filtration (One-Step Addition) | Filtration (Multiple-Step Addition) |
| $HNO_3$ (as 100% $HNO_3$), Gms | 49.0 | 49.0 | 49.0 | 49.0 |
| Coal (Moisture-free and Ash-free) Gms | 51.0 | 51.0 | 51.0 | 51.0 |
| $H_2O$, Gms | 136 | 136 | 136 | 136 |
| Total Organic Product, Gms | 65.5 | 67.0 | 61.4 | 64.1 |
| Coal Converted to Solvent-Soluble Coal Acids, Gms | 30.7 | 27.3 | 19.5 | 18.0 |
| Coal Intermediates Not Converted to Solvent-Soluble Coal Acids, Gms | 20.3 | 23.7 | 31.5 | 33.0 |
| Solvent-Soluble Coal Acids, Gms | 40.9 | 39.0 | 25.4 | 26.2 |
| Water-Soluble Coal Acids, Gms | * | * | 7.3 | 8.6 |
| Solvent-Soluble Coal Acids, Yield Percent | 130.6 | 139.7 | 125.1 | 140.8 |
| Coal Converted to Solvent-Soluble Coal Acids, Percent | 60.6 | 54.0 | 39.3 | 36.0 |
| Nitric Acid Consumed (as 100% $HNO_3$), Weight Percent | 88.0 | 88.0 | 64.0 | 65.0 |
| Nitric Acid Concentration in Filtrate or Water Distillate, Percent | 4.2 | 4.2 | 11.5 | 11.2 |

*Not Recovered separately; included in solvent-soluble coal acids.

The unexpected results obtained following the dictates of the novel process defined and claimed herein are apparent from an examination of the data in the above table. Examples I and II were similar to Examples III and IV, respectively, except that while in the first two examples the reaction products were subjected to evaporation to remove water therefrom, the latter two examples were subjected to filtration, as in U.S. Pat. No. 4,052,448, referred to above. While coal conversions in Examples I and II were 60.6 and 54.0 percent, respectively, in Examples III and IV coal conversions of but 39.3 and 36.0, respectively, were obtained. Yet, unexpectedly, yields to desired carboxylic acids were not adversely affected. Additionally, while nitric acid utilization in each of Examples I and II was 88 percent, in Examples III and IV nitric acid utilization effected in the temperature range of about 50° to about 100° C. for about two to about six hours.

4. The process of claim 1 wherein said drying is effected at a pressure of about atmospheric to about one millimeter of mercury and a temperature of about 50° to about 100° C.

5. The process of claim 1 wherein upon completion of said drying the remainder of the product is subjected to extraction with a polar solvent to recover solvent-soluble monocyclic, polycyclic multi-functional carboxylic acids.

6. The process of claim 5 wherein said polar solvent is methanol.

7. The process of claim 5 wherein said polar solvent is ethanol.

8. The process of claim 5 wherein said polar solvent is acetone.

9. The process of claim 1 wherein upon completion of said drying the remainder of the product is subjected to extraction with a combination of polar solvents.

10. The process of claim 9 wherein said combination of polar solvents includes methanol and ethanol.

11. The process of claim 9 wherein said combination of polar solvents includes at least one of methanol and ethanol with acetone.

12. The process of claim 9 wherein said combination of polar solvents includes water.

13. The process of claim 9 wherein said combination of polar solvents includes at least one of methanol, ethanol, acetone and tetrahydrofuran with water.

14. The process of claim 1 wherein only about 60 to about 90 weight percent of the coal to be treated is present at the beginning of the reaction and the remainder is added prior to the termination of the reaction.

15. The process of claim 1 wherein only about 70 to about 80 weight percent of the coal to be treated is present at the beginning of the reaction and the remainder is added prior to the termination of the reaction.

16. The process of claim 14 wherein the subsequent addition of coal is made within a period of about 0.5 to about 10 hours following the principal reaction period.

17. The process of claim 15 wherein the subsequent addition of coal is made within a period of about one to about five hours following the principal reaction period.

* * * * *